United States Patent [19]

Telschow et al.

[11] Patent Number: 4,713,467

[45] Date of Patent: Dec. 15, 1987

[54] PROCESS FOR PRODUCTION OF ISOTHIOCYANATES

[75] Inventors: Jeffrey E. Telschow, Tarrytown; Danielle A. Bright, Spring Valley, both of N.Y.

[73] Assignee: Stauffer Chemical Company, Westport, Conn.

[21] Appl. No.: 927,478

[22] Filed: Nov. 6, 1986

[51] Int. Cl.$^4$ .................................... C07C 161/04
[52] U.S. Cl. ...................................... 558/18
[58] Field of Search ............................ 558/18

[56] References Cited

U.S. PATENT DOCUMENTS

| | | | |
|---|---|---|---|
| 2,859,235 | 11/1958 | Schmidt et al. | 558/18 |
| 2,859,236 | 11/1958 | Schmidt et al. | 558/18 |
| 3,234,254 | 2/1966 | Söder et al. | 558/18 |
| 3,404,171 | 10/1968 | Ulrich | 558/18 |
| 3,637,788 | 1/1972 | Werth et al. | 558/18 |
| 3,787,472 | 1/1974 | Giesselmann et al. | 558/18 |
| 3,923,852 | 12/1975 | Zeiler et al. | 558/18 |
| 3,923,853 | 12/1975 | Zeiler | 558/18 |

FOREIGN PATENT DOCUMENTS 892790  3/1962  United Kingdom ............... 558/18

OTHER PUBLICATIONS

Chem. Abstracts, vol. 1, 2236.

*Primary Examiner*—Henry R. Jiles
*Assistant Examiner*—Robert C. Whittenbaugh
*Attorney, Agent, or Firm*—Richard P. Fennelly

[57] ABSTRACT

Isothiocyanates are formed by oxidizing, with gaseous oxygen or air, in the presence of a metal oxidation catalyst a dithiocarbamate with appropriate control of the pH of the reaction medium to suppress the formation of by-products. Optionally a quaternary ammonium halide catalyst can be used to increase product yield.

10 Claims, No Drawings

4,713,467

PROCESS FOR PRODUCTION OF ISOTHIOCYANATES

BACKGROUND OF THE PRESENT INVENTION

1. Field of the Invention

The present invention is an improved process for the production of isothiocyanates.

2. Description of the Prior Art

In U.S. Pat. No. 3,923,852, a process for preparing isothiocyanates is described wherein an amine and carbon disulfide are reacted with gaseous oxygen in the presence of a metal as an oxidation catalyst.

The process of the present invention utilizes the same oxidant as used in the aforementioned patent in conjunction with the same type of catalyst. However, a different starting material is used and the pH of the reaction medium is controlled to suppress the formation of undesired by-products thereby improving the yield of the desired isothiocyanate.

SUMMARY OF THE PRESENT INVENTION

The present invention involves the formation of isothiocyanates utilizing an oxygen-containing gas as an oxidant in conjunction with a metal oxidation catalyst wherein the pH of the reaction medium is controlled to suppress the undesired formation of by-products and to improve the reaction yield. A phase transfer catalyst may be used to improve product yield.

DETAILED DESCRIPTION OF THE PRESENT INVENTION

The present invention is directed to the formation of isothiocyanates which are a known class of compound having the formula RNCS, where R can be an organo moiety, for example, an aliphatic moiety (e.g., alkyl or cycloalkyl) or aromatic. Representative alkyl moieties include such lower alkyl groups such as methyl and butyl or, in the case of cycloalkyl, cyclohexyl.

The oxidant that is used in conjunction with the present invention is the same oxidant that is used in the aforementioned patent, namely, gaseous oxygen or air as the oxygen-containing gas. The use of such an oxidant is especially desirable since it does not add any chemical compound to the reaction mixture which would possibly unnecessarily complicate the type of by-product that is formed or is present.

In accordance with the general procedure shown in the aforementioned patent, the present invention also utilizes a metal oxidation catalyst of the general type shown in that patent. Representative oxidation catalysts include such metals as manganese, iron, copper, zinc, cobalt and molybdenum or one or more of the water-soluble salts of such metals. Generally speaking, the amount of such a catalyst is present anywhere from about 0.005% to about 0.5% by weight of the reaction mixture.

In accordance with the aforementioned patent, it is also possible to use a non-aqueous solvent in the reaction medium such as carbon tetrachloride, benzene, methylene chloride or chloroform in order to assist in the recovery of the desired isothiocyanate product.

The temperature under which the present process can be practiced can be varied over a wide range. Representative temperatures of up to about 200° C., the boiling point of water can be used. The temperature used can be higher than that shown in U.S. Pat. No. 3,923,852 since mixtures of $CS_2$ and oxygen are not present.

The point of departure for the present invention from the aforementioned patent is at least threefold. The first is the use of a dithiocarbamate starting reactant rather than the primary amine and carbon disulfide reactants taught by the patent. Preferably, the alkali metal salt of the corresponding dithiocarbamate is the desired starting material for use in the present invention. For example, the sodium salt of n-butyl dithiocarbamate is desired if the intended product is n-butyl isothiocyanate. Nonuse of $CS_2$ as a reactant, in conjunction with the oxygen-containing gas, removes the danger of flammability which exists in regard to the process shown in U.S. Pat. No. 3,923,852 where these two reactants are present throughout the process. Mixtures of $CS_2$ and oxygen can spontaneously inflame at temperatures of about 35° C. and above.

A second point of departure for the present invention is the discovery that pH control is important in regard to the present process if one wishes to suppress the formation of undesirable by-product, e.g., N,N'-dibutyl-thiourea when n-butyl isothiocyanate is the desired end product. Generally speaking, a pH of from about 10.5 to 12 is most preferred, for example, for n-butyl isothiocyanate and a pH of 8.5–9.5 for methyl isothiocyanate if the best yields and reaction rates are desired. At pH values over 12 for the n-butyl product (and over 10 for the methyl product) the reaction rate begins to slow, apparently due to formation of insoluble metal hydroxides or oxides from the metal catalyst. As the pH drops, the extent of decomposition of the starting dithiocarbamate salt to a primary amine (and $CS_2$) increases. The reaction of the liberated amine, $RNH_2$, with the product, RNCS, gives rise to the dialkylthiourea by-product, RNHC(S)NHR, for example.

A third point of departure of the present invention is the avoidance of the use of ammonia or excess amine in the reaction mixture. In this way, the formation of mono- or dialkylthioureas, respectively, for example, is avoided or reduced.

A fourth point of departure is the optional use of a phase transfer catalyst to increase the yield of product when a non-aqueous solvent is used, as described earlier. One class of catalyst that can be used is the quaternary ammonium halides such as those containing four $C_1$–$C_{10}$ groups with the halide being chloride. The amount of catalyst used can range from about 0.1% to about 5%, by weight of the reactants.

The foregoing represents certain embodiments of the present invention and the invention is further illustrated with the Examples which follow.

EXAMPLES 1–5

An aqueous solution containing 0.2 mole of sodium n-butyl dithiocarbamate was treated with 40 mg of $MnCl_2$, 300 mg of 1,2,4,5-tetrachlorobenzene (an internal standard for gas chromatographic (gc) analysis) and 50 ml of $CHCl_3$. The reactor was fitted with a dropping funnel containing 0.2 mole of either concentrated hydrochloric (HCl) or acetic (HOAc) acid, a pH electrode, a pot thermometer, and a fritted gas dispersion tube. The stirred reaction mixture was treated under slight pressure with oxygen gas, and acid was added dropwise to maintain the desired pH range. Temperature was maintained at 20°–25° C. with a cool water bath. When the reaction was complete, the yield of n-butyl isothiocyanate (BuNCS) was estimated by gc analysis. The pH range of 10.5 to 12 seems optimum since the reaction rate slows at pH >12.

| Yield of BuNCS vs pH | | |
|---|---|---|
| Acid | pH | Estimated Yield |
| HCl | 7.5–8.5 | 43% |
| HCl | 9.5–10.5 | 67% |
| HCl | 10.5–11.5 | 75% |
| HCl | 11.5–12 | 75.5% |
| HOAc | 10.5–11 | 79% |

For comparison, when $BuNHCS_2NH_4$ was oxidized in a manner analogous to U.S. Pat. No. 3,923,852, the best yield was 68%. Also, much undesirable by-product butylthiourea was produced, and it is absent when the sodium salt is used in the process of the present invention.

EXAMPLE 6

Into a two-liter 4-necked flask was placed 2.5 moles (428 g.) of sodium N-butyldithiocarbamate in 340 ml. of water. To the resulting slurry was added 300 ml. of $CHCl_3$ and 500 mg of $MnCl_2$. The reaction mixture was stirred rapidly, the system was closed, and oxygen gas was allowed to flow in under 1–2 obs. of pressure through a fritted bubbler. The pH began to rise from an initial value of 11.3 and was maintained at 11.8±0.5 by the addition of concentrated HCl (175 ml.) over the course of the six-hour reaction. The reaction temperature was maintained at 27°–34° C.

The organic phase was then separated, the $CHCl_3$ was removed via rotary evaporator, and the product was distilled as a colorless liquid: b.p.: 75° C./20 mm (259.6 g./90.1% yield). It was 99.8 area percent pure butyl isothiocyanate by gc analysis.

EXAMPLE 7

The procedure of Example 6 was repeated except that 7 molal $H_2SO_4$ was used instead of HCl and 672 mg of $MnSO_4.H_2O$ replaced the $MnCL_2$. The yield was 89.4%.

EXAMPLE 8

The procedure of Example 7 was used to prepare cycohexylisothiocyanate from sodium N-cyclohexyldithiocarbamate (2.5 moles). The reaction temperature was 30° C.–50° C. The yield of product was 89.7% (316.1 gm): b.p.: 85° C./4 mm; 99.8 area percent pure by gc analysis.

EXAMPLES 9–15

An aqueous solution containing 0.48 mole of sodium methyldithiocarbamate was treated with 270 mg of $MnSO_4.H_2O$ and 100 ml of $CH_2Cl_2$. In Examples 10, 12 and 14, 500 mg of a phase transfer catalyst was also added to the reaction mixture. The catalyst used was ALIQUAT 336, tricaprylyl methylammonium chloride. The reactor was fitted with a dropping funnel containing 0.24 mole of 7 molal sulfuric acid, a pH electrode, a pot thermometer and a fritted gas dispersion tube.

The stirred reaction mixture was treated under slight pressure with oxygen gas, and acid was added dropwise to maintain the desired pH range. The reaction temperature was kept at 25°–30° C. Upon completion of the reaction, the sulfur by-product was filtered and the layers separated. The aqueous layer was extracted with 50 ml of $CH_2Cl_2$ and 2×25 ml of $CH_2Cl_2$. The combined organic layers were distilled to give the following yields of methyl isothiocyanate (MITC) having a boiling point of 115°–117° C.:

| Example No. | pH | % Yield MITC |
|---|---|---|
| 9 | 8.5–9 | 70 |
| 10 | 8.5–9 | 89 |
| 11 | 9–9.5 | 75 |
| 12 | 9–9.5 | 90 |
| 13 | 9.5–10 | 69 |
| 14 | 9.5–10 | 74 |
| 15 | 10–10.5 | 28 |

The pH range of 8.5–9.5 seems to be preferred. The addition of phase transfer catalyst in Examples 10, 12 and 14 led to increased yield.

The foregoing Examples should not be construed in a limiting sense since they are merely set forth to illustrate certain preferred embodiments of the present invention. The claims which follow set forth the scope of protection that is desired.

We claim:

1. A process for forming an isothiocyanate which comprises oxidizing, with an oxygen-containing gas, a dithiocarbamate in the presence of a metal oxidation catalyst with adjustment of the pH to suppress the formation of undesired by-product.

2. A process as claimed in claim 1 wherein the gas is air.

3. A process as claimed in claim 1 wherein substantially pure oxygen is the gas.

4. A process as claimed in claim 1 wherein the pH ranges from about 8.5 to about 12.

5. A process as claimed in claim 1 wherein the dithiocarbamate is an alkyl dithiocarbamate and the pH ranges from about 8.5 to about 12.

6. A process as claimed in claim 1 wherein the dithiocarbamate is a cycloalkyl dithiocarbamate and the pH ranges from about 8.5 to about 12.

7. A process as claimed in claim 5 wherein the gas is air.

8. A process as claimed in claim 6 wherein substantially pure oxygen is the gas.

9. A process as claimed in claim 1 which further comprises the use of a quaternary ammonium halide catalyst.

10. A process as claimed in claim 9 wherein the catalyst contains four $C_1$–$C_{10}$ alkyl groups.

* * * * *

UNITED STATES PATENT AND TRADEMARK OFFICE
CERTIFICATE OF CORRECTION

PATENT NO. : 4,713,467
DATED : December 15, 1987
INVENTOR(S) : Jeffrey E. Telschow et al.

It is certified that error appears in the above-identified patent and that said Letters Patent is hereby corrected as shown below:

In column 1, at line 67, the number "200°C" should read --- 100°C ---.

In column 3, at line 26, the word "obs." should read --- lbs. ---.

In column 3, at line 41, the phrase "MnCL$_2$" should read --- MnCl$_2$ ---.

Signed and Sealed this

Third Day of January, 1989

Attest:

DONALD J. QUIGG

*Attesting Officer*      *Commissioner of Patents and Trademarks*